(12) United States Patent
Harandi et al.

(10) Patent No.: US 10,399,913 B2
(45) Date of Patent: Sep. 3, 2019

(54) UPGRADING PARAFFINS AND OLEFINS

(71) Applicant: ExxonMobil Research and Engineering Company, Annandale, NJ (US)

(72) Inventors: Mohsen N. Harandi, New Hope, PA (US); John Dusseault, Sarnia (CA)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/217,097

(22) Filed: Dec. 12, 2018

(65) Prior Publication Data

US 2019/0194088 A1 Jun. 27, 2019

Related U.S. Application Data

(60) Provisional application No. 62/608,688, filed on Dec. 21, 2017.

(51) Int. Cl.

| | |
|---|---|
| *C07C 2/06* | (2006.01) |
| *C07C 2/54* | (2006.01) |
| *C07C 2/64* | (2006.01) |
| *C07C 2/12* | (2006.01) |
| *C07C 9/14* | (2006.01) |

(Continued)

(52) U.S. Cl.
CPC .............. *C07C 2/12* (2013.01); *B01J 8/005* (2013.01); *B01J 8/0015* (2013.01); *B01J 8/1827* (2013.01); *B01J 8/1863* (2013.01); *C07C 5/333* (2013.01); *C07C 9/14* (2013.01); *C10L 1/06* (2013.01); *B01J 2208/00752* (2013.01); *B01J 2208/00761* (2013.01); *B01J 2208/00769* (2013.01); *B01J 2208/00893* (2013.01);
(Continued)

(58) Field of Classification Search
CPC ................ C07C 2/06; C07C 2/54; C07C 2/64
USPC ........ 585/324, 326, 329, 332, 446, 407, 654
See application file for complete search history.

(56) References Cited

U.S. PATENT DOCUMENTS

| | | |
|---|---|---|
| 3,845,150 A | 10/1974 | Yan et al. |
| 4,016,218 A | 4/1977 | Haag et al. |

(Continued)

OTHER PUBLICATIONS

The International Search Report and Written Opinion of PCT/US2018/065064 dated Apr. 9, 2019.

*Primary Examiner* — Thuan D Dang
(74) *Attorney, Agent, or Firm* — Priya G. Prasad

(57) ABSTRACT

In a process for upgrading paraffins and olefins, a first feed comprising $C_{14-}$ olefins is contacted with an oligomerization catalyst in a first reaction zone under conditions effective for oligomerization of olefins to higher molecular weight hydrocarbons. Deactivated catalyst is removed from the first reaction zone at a first temperature and is contacted with an oxygen-containing gas and a hydrocarbon-containing fuel in a regeneration zone to regenerate the catalyst and raise the temperature of the catalyst to a second, higher temperature. A second feed comprising $C_{14-}$ paraffins is contacted with the regenerated catalyst in a second reaction zone to convert at least some of the paraffins in the second feed to a reaction effluent comprising olefins, aromatic hydrocarbons and regenerated catalyst; and the reaction effluent is supplied to the first reaction zone. A system for performing such a process and a product of such a process are also provided.

14 Claims, 1 Drawing Sheet

(51) Int. Cl.
*C10L 1/06* (2006.01)
*B01J 8/18* (2006.01)
*B01J 8/00* (2006.01)
*C07C 5/333* (2006.01)

(52) U.S. Cl.
CPC .... *C07C 2529/06* (2013.01); *C10L 2270/023* (2013.01); *C10L 2290/12* (2013.01)

(56) References Cited

U.S. PATENT DOCUMENTS

| | | |
|---|---|---|
| 4,788,364 A | 11/1988 | Harandi |
| 4,868,145 A | 9/1989 | Dessau et al. |
| 4,956,510 A | 9/1990 | Harandi |
| 4,990,710 A | 2/1991 | Dessau et al. |
| 8,470,165 B2 | 6/2013 | Cosyns et al. |
| 9,598,649 B2 | 3/2017 | Nagabhatla et al. |
| 2008/0172931 A1 | 7/2008 | Bazzani et al. |
| 2011/0257452 A1* | 10/2011 | Khabashesku ........... B01J 23/06 585/418 |
| 2016/0264492 A1 | 9/2016 | Smalley et al. |

* cited by examiner

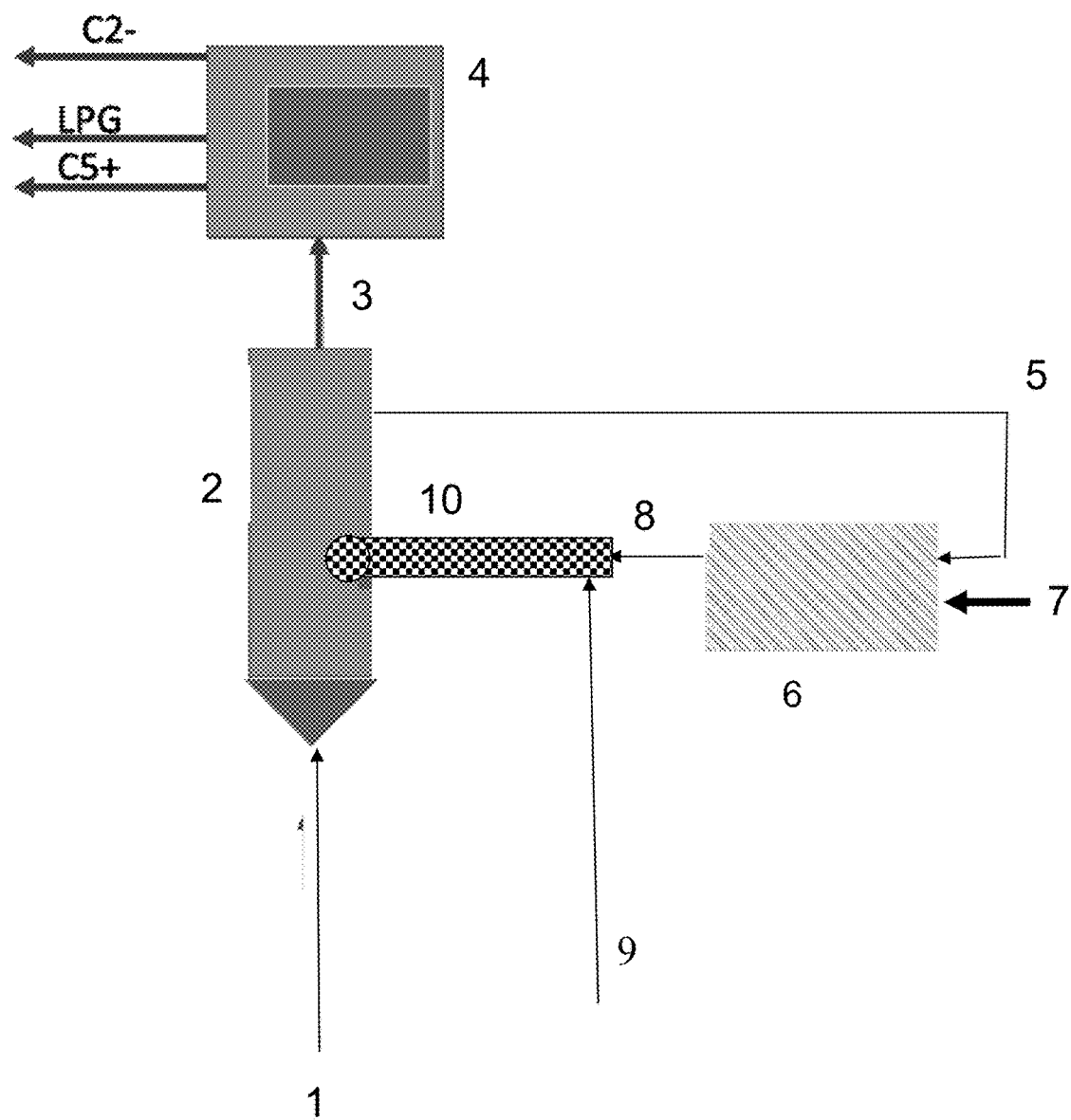

UPGRADING PARAFFINS AND OLEFINS

CROSS-REFERENCE TO RELATED APPLICATIONS

This application claims the benefit of U.S. Provisional Application No. 62/608,688, filed on Dec. 21, 2017, the entire contents of which are incorporated herein by reference.

FIELD

The present disclosure is directed to a process and system for upgrading paraffins and olefins to produce gasoline and distillate boiling-range hydrocarbons.

BACKGROUND

For several decades the fuels industry has tried to improve the economics of olefins oligomerization as a means to make gasoline and diesel. However, the yield and overall economics of alternative processes, especially isoparaffin-olefin alkylation, have been too challenging mainly because alkylation also upgrades iso-$C_4$ hydrocarbons in available refinery feedstocks and produces a higher quality product.

Similarly, researchers have tried to make processes for upgrading light paraffins more economical. However, although there is an over-supply of light paraffins in the market and margins are attractive, the high cost, mainly due to the endothermic nature of the reaction, as well as low yield have prevented much commercial application of this important chemistry. In fact, light olefins, and particularly light paraffins upgrading, is one of the highest margin improvement upgrading technologies per barrel of feed. Margin uplift can be as high $15-30/BBL. However, current technologies have failed to capture much of this potential.

There is therefore a need in the art of fuels refining for an economically viable process to incorporate paraffins into the feedstocks used in the oligomerization of olefins for commercial gasoline and diesel production. There is also interest in minimizing the benzene content of the product.

U.S. Pat. No. 3,845,150 discloses a process for the aromatization of hydrocarbon streams over a ZSM-5 catalyst in which the heat input requirements normally associated with the aromatization of saturated hydrocarbons is substantially eliminated by combining the saturated hydrocarbon feed with an unsaturated hydrocarbon feed such that the combined feed contains 20 to 65 weight % of reactive saturates and 20 to 50 weight % of olefins. The process is conducted at a temperature of 650 to 1500° F. (343 to 816° C.) and a weight hourly space velocity of 0.1 to 15 in the absence of added hydrogen. However, the process suffers from the disadvantage that the conversion conditions are necessarily a compromise between the optimal conditions for upgrading the reactive saturates and optimal conditions for upgrading the olefins. As a result, the yields of the desired products are low.

U.S. Pat. No. 4,788,364, hereby incorporated by reference, discloses an improved two-step process for the conversion of lower molecular weight paraffins, the process comprising contacting in a first step a $C_2$-$C_{10}$ alkane-rich feedstock with a siliceous zeolite catalyst in a primary fluidized bed reaction zone under high temperature dehydrogenation conditions to obtain an intermediate product comprising oligomerizable olefinic hydrocarbons and aromatics; and then contacting in a second step the intermediate product with a siliceous zeolite catalyst in a secondary fluidized bed reaction zone under low temperature oligomerization conditions to obtain a final product comprising gasoline boiling range aliphatic and aromatic hydrocarbons. Thermal balance is maintained by employing a heat exchange line containing steam or preheated feedstock. However, the addition of steam can deactivate the zeolite catalyst while preheating the feed can lead to cracking and hence fouling of the feed preheater.

SUMMARY

In one aspect, the present disclosure resides in a process for upgrading paraffins and olefins, the process comprising:

i) contacting a first feed comprising $C_{14-}$ olefins with an oligomerization catalyst in a first reaction zone under conditions effective for oligomerization of olefins to higher molecular weight hydrocarbons;

ii) removing deactivated catalyst from the first reaction zone at a first temperature;

iii) contacting the deactivated catalyst with an oxygen-containing gas and with a hydrocarbon-containing fuel in a regeneration zone to regenerate the catalyst and raise the temperature of the catalyst to a second, higher temperature;

iv) contacting a second feed comprising $C_{14-}$ paraffins with the regenerated catalyst in a second reaction zone to convert at least some of the paraffins in the second feed to a reaction effluent comprising olefins, aromatic hydrocarbons and regenerated catalyst; and v) supplying the reaction effluent to the first reaction zone.

In a further aspect, the present disclosure resides in a system for upgrading paraffins and olefins comprising:

an oligomerization reactor containing a fluidized catalyst and configured with separate inlets to receive a converted paraffin feed stream comprising regenerated catalyst and a fresh olefin feed stream and further configured with separate outlets for a product stream and a spent catalyst stream;

a catalyst regenerator configured with an inlet to receive a spent catalyst stream from the oligomerization reactor, an inlet for an oxidant gas and an inlet for receiving a fuel, and configured with an outlet for a regenerated catalyst stream; and a mixing zone configured to combine a fresh paraffinic feed stream with the regenerated catalyst stream and having an outlet for a converted paraffin feed stream; and a transfer line connecting the mixing zone to the converted paraffin feed stream inlet of the oligomerization reactor.

In yet a further aspect, the present disclosure resides in a $C_{5+}$ hydrocarbon product produced by integrating a process of oligomerizing an olefinic feed under a first set of conditions and a process of dehydrocyclizing a paraffinic feed under a second set of conditions, the product containing less benzene than would be produced by dehydrocyclizing the paraffinic feed alone under the second set of conditions.

BRIEF DESCRIPTION OF THE DRAWINGS

FIG. 1 is a schematic illustration of an integrated system according to one embodiment of the invention for upgrading paraffins and olefins to $C_{5+}$ products.

DETAILED DESCRIPTION

Disclosed are a process and system for upgrading paraffins and olefins to gasoline and distillate boiling-range hydrocarbons by integrating paraffin dehydrogenation and dehydrocyclization with olefin oligomerization in a way that allows balancing the heat requirements of both processes while ensuring that each process can be operated under optimal conditions. In particular, in the present process a first feed comprising $C_{14-}$ olefins is contacted with an oligomerization catalyst in a first reaction zone under conditions effective to partially oligomerize olefins to higher molecular weight hydrocarbons. The conditions preferably also provide for alkylating aromatics present in the process stream within the first reaction zone. The extent of conversion of olefins by oligomerization can be controlled to optimize benzene alkylation in the first reaction zone.

As the oligomerization and alkylation reactions proceed in the first reaction zone, carbonaceous material, also referred to herein as coke, is deposited on the catalyst. Coked catalyst is continuously or intermittently removed from the first reaction zone at a first temperature T1 and contacted with an oxygen-containing gas in a regeneration zone to regenerate and raise the temperature of the catalyst. An external source of hydrocarbon fuel is also added to the regenerator so that the regeneration process can raise the temperature of the regenerated catalyst to a second, higher temperature T2 optimized for dehydrogenation and dehydrocyclization of paraffins to a product containing olefins and aromatics.

The freshly regenerated catalyst is then contacted with a second feed comprising $C_{14-}$ paraffins in a second reaction zone to convert at least some of the paraffins in the second feed to produce a reaction effluent comprising olefins, aromatic hydrocarbons and regenerated catalyst, which is at a third temperature T3 less than T2, but typically about the same or greater than T1. In a preferred embodiment, where the second reaction zone comprises a well-mixed fluidized reaction bed arranged to operate isothermally, T3 will normally equal T1. In other embodiments, where the second reaction zone employs a riser reactor or a moving bed reactor instead of the fluid-bed then the second reaction is more adiabatic and, since the reactions occurring in the second reaction zone are also exothermic, the heat of reaction increases T3 above T1.

The dehydrogenation and dehydrocyclization reaction effluent is then supplied to the first reaction zone where the olefins in the reaction effluent are oligomerized along with the olefins in the first feed. At least some of the olefins also alkylate the aromatic hydrocarbons, especially benzene, in the reaction effluent so that the product of the first reaction zone normally has a significantly lower benzene content than would be obtained by dehydrocyclization of the second feed under the conditions in the second reaction zone. By controlling the weight ratio of the amount of $C_{14-}$ olefins in the first feed to the amount of $C_{14-}$ paraffins in the second feed, it is possible to ensure that the reaction product of the first reaction zone contains less than 10 wt. % benzene, such as less than 4 wt. % benzene, preferably less than 1 wt. % benzene. Typically, the volume ratio of the amount of $C_{14-}$ olefins containing feed to the amount of $C_{14-}$ paraffins in the second feed is selected to be at least 0.1:1, such as at least 0.5:1, preferably at least 1:1 but in most cases is maintained at a value of less than 100:1.

In one embodiment, the present disclosure provides a novel system for upgrading paraffins and olefins by integrating paraffin dehydrocyclization with olefin oligomerization. The system comprises an oligomerization reactor which contains a fluidized catalyst and which is configured with separate inlets to receive a converted paraffin feed stream comprising regenerated catalyst and a fresh olefin feed stream and further configured with separate outlets for a product stream and a spent catalyst stream. Connected to the oligomerization reactor is a catalyst regenerator configured with an inlet to receive the spent catalyst stream from the oligomerization reactor and with inlets for an oxidant gas and a hydrocarbon fuel, preferably fuel gas or natural gas. The catalyst regenerator has an outlet for a regenerated catalyst stream that is connected to a mixing zone which is configured to combine the regenerated catalyst stream with a fresh paraffinic feed stream and which has an outlet for the converted paraffin feed stream. A transfer line connects the mixing zone to the converted paraffin feed stream inlet of the oligomerization reactor.

Feeds

Any paraffin or olefin feed comprising $C_{14-}$ paraffins or olefins can be used as the first and second feeds, respectively, in the present process. However, methane is not upgraded to other hydrocarbons in the present process. In this respect, it is to be appreciated that the term "$C_n$" compound (olefin or paraffin) wherein n is a positive integer, e.g., 1, 2, 3, 4, 5, etc, means a compound having n number of carbon atom(s) per molecule. The term "$C_{n+}$" compound wherein n is a positive integer, e.g., 1, 2, 3, 4, 5, etc, means a compound having at least n number of carbon atom(s) per molecule. The term "$C_{n-}$" compound wherein n is a positive integer, e.g., 1, 2, 3, 4, 5, etc, as used herein, means a compound having no more than n number of carbon atom(s) per molecule.

The preferred paraffin feeds are those in the $C_2$-$C_{10}$ range, or the $C_2$-$C_8$ range, especially $C_3$-$C_5$ paraffins, such as n-butane. A suitable paraffinic feed is described in US Patent Application Publication No. 2016/264492, which is hereby incorporated by reference. Saturated gas plant Liquid Petroleum Gas (LPG) and reformer paraffins are described as suitable paraffinic in U.S. Pat. No. 4,788,364, which is hereby incorporated by reference.

Preferred olefin feeds are those in the $C_2$-$C_8$ range. Olefins can be added individually or as mixtures. In various aspects, the olefin-containing feed can include at least about 10 wt %, at least about 20 wt %, at least about 30 wt %, at least about 40 wt %, at least about 50 wt %, or at least about 60 wt % olefins. In the same or alternative aspects, the olefin-containing feed can include up to 100% olefins, but typically will include less than about 100 wt %, less than about 90 wt %, less than about 80 wt %, or less than about 70 wt % olefins. Suitable olefin-containing feeds include one or more low value refinery streams, such as refinery fuel gas or flue gas from a cracking or coking process, for example FCC fuel gas. Other preferred feeds include olefinic LPG and/or any fraction of cracked naphthas, particularly light FCC and/or coker naphtha. Feeds like cracked naphtha contain sulfur and in the presently disclosed process, at least a significant part of any organic sulfur and nitrogen in the feed is converted to $H_2S$ and $NH_3$ without addition of any $H_2$ feed. The paraffinic feeds such as natural gasoline or light straight run gasoline also are purified by converting its sulfur and nitrogen compounds in the same manner.

Olefin Oligomerization

The olefin oligomerization stage of the present process can be performed at a temperature of 600-900° F. (316-482° C.), preferably from 650-800° F. (343-427° C.). The unit pressure is typically 20-400 psig, and in some embodiments is around 50-180 psig. In some embodiments, the olefin oligomerization stage is conducted in a riser reactor or a fluid bed reactor.

In the olefin oligomerization reactor, olefins added in the first feed are reacted with olefins generated from paraffins in the second feed and also with aromatics (especially benzene) made from paraffins in the second feed to produce a gasoline and/or distillate boiling-range product with a very low, typically less than 1 wt. %, benzene content. In addition, some coke is generated on the oligomerization catalyst and so the catalyst is continuously or intermittently removed from the oligomerization reaction zone and supplied to a regeneration zone, where the coke is burnt from the catalyst by contact with an oxygen-containing gas. The temperature of the catalyst is thereby increased but, even though the oligomerization reaction is exothermic, this is insufficient to raise the catalyst temperature to the optimum value for paraffin dehydrogenation. Thus, a hydrocarbon-containing fuel, such as natural gas, fuel gas, LPG, liquid fuel, solid fuel or part of the paraffin feed, is also supplied to the regeneration zone to further raise the temperature of the catalyst. In this way, the temperature of the oligomerization catalyst is raised by at least 150° C. in the regeneration zone. For example, if the temperature of the catalyst leaving the oligomerization zone is at a first value, $T1$, in the range 300 to 400° C., the temperature of the catalyst leaving the regeneration zone will preferably be at a second, higher temperature of 649 to 760° C. (1200 to 1400° F.). Since the freshly regenerated catalyst is then fed directly to the paraffin dehydrogenation zone, this sets the initial temperature of the endothermic paraffin conversion reaction.

Paraffin Dehydrogenation and Dehydrocyclization

Paraffin dehydrogenation and dehydrocyclization conditions employed in the present process broadly include temperatures of about 480 to 710° C. (900 to 1400° F.). More typically, the temperature of the catalyst, at least at the inlet to paraffin conversion zone is from about 650 to 790° C. (1200 to 1450° F.). The pressure condition is typically from 100 to 2000 kPa (14 to 275 psig). The pressure will typically be the same as that used for the olefin oligomerization reaction (which is usually in the range from 20-400 psig (240 to 2860 kPa-a), but this is not required. Flow rate through the paraffin dehydrocylization reaction zone is at a WHSV of 0.1 to 100 $hr^1$. The space velocity required to achieve the desired extent of dehydrogenation will depend upon, among other factors, the feed composition and the temperature of the regenerated catalyst bed.

The paraffin dehydrogenation and dehydrocyclization reaction can be conducted in any convenient reaction zone, including a riser reactor or a fluid bed reactor separate from the oligomerization reactor. More preferably, however, the paraffin conversion reaction is conducted in a transfer line used to supply the freshly regenerated catalyst from the regeneration zone to the oligomerization reactor.

A number of chemical reactions, such as dehydrogenation, oligomerization, iso-paraffin/olefin alkylation, and aromatization, occur in the paraffin conversion reaction zone thereby converting the paraffin feed to a mixture of olefins and aromatic hydrocarbons. Overall, the paraffin conversion reactions are endothermic and so the reaction effluent leaving the second reaction zone is typically at a temperature from 915 to 1200° F. (490 to 650° C.), preferably from 950 to 1100° F. (510-593° C.). In addition to ontrolling th supply of external fuel to th the regenerator, the temperatures in the first and second reaction zones can be controlled by preheating of the olefinic feed and/or steam generation either inside the fluid-bed or in a catalyst cooler.

At a point prior to or along the length of the oligomerization reaction zone, the reaction effluent from the second reaction zone, including the regenerated catalyst, is mixed with the olefin-containing feed. The position of the supply of the paraffins conversion effluent to the oligomerization reactor can be adjusted from the very bottom to the very top of the reactor or even above the fluid bed or even into a cyclone inlet depending on the extent of the reaction desired for aromatic and olefinic intermediates in the paraffins conversion effluent. A lower location results in a lower benzene in the product leaving the oligomerization reactor and reduced light olefins production.

Catalysts

Catalysts useful in the presently disclosed methods and systems are those that have both of paraffin dehydrogenation activity and hydrocarbon oligomerization activity. In preferred embodiments, the same catalyst (or the same mixture of catalysts) is used for to all of the hydrocarbon conversion reactions.

Paraffin dehydrogenation catalysts include oxides and sulfides of the elements of Groups IVA, VA, VIA, VIIA and VIIIA of the Periodic Table and mixtures thereof on an inert support such as alumina or silica-alumina. Thus, dehydrogenation may be promoted by sulfides and oxides of titanium, zirconium, vanadium, niobium, tantalum, chromium, molybdenum, tungsten and mixtures thereof. Oxides of chromium alone or in conjunction with other catalytically active species have been shown to be particularly useful in dehydrogenation. Other catalytically active compounds include sulfides and oxides of maganese, iron, cobalt, rhodium, iridium, nickel, palladium, platinum and mixtures thereof.

The above-listed metals of Groups IVA, VA, VIA, VIIA and VIIIA may also be exchanged onto zeolites to provide a zeolite catalyst having dehydrogenation activity. A catalyst for the oligomerization reactions can include a medium or smaller pore zeolite catalyst, such as exemplified by at least one of ZSM-5, ZSM-11, ZSM-12, ZSM-23, ZSM-35, ZSM-38, ZSM-48, and other similar materials. Other suitable medium or smaller pore zeolites include ferrierite, and erionite. A preferred catalyst for both paraffins conversion and olefins conversions is a zeolite or a silica-aluminum phosphate (SAPO) with metal(s) promotion or without. One preferred promoter is phosphorous. Other preferred promoters are Zn, Ga and/or Ni.

The zeolite or SAPO can be dispersed on a matrix including a binder material such as silica or alumina and an inert filler material such as kaolin. These catalysts may have a crystalline zeolite or SAPO content of about 10 to about 50 wt % or more, and a matrix material content of about 50 to about 90 wt %. Catalysts containing at least about 40 wt % crystalline zeolite material are typical, and those with greater crystalline zeolite content may be used. Generally, medium and smaller pore zeolites are characterized by having an effective pore opening diameter of less than or equal to about 0.7 nm and rings of about 10 or fewer members. Molecular sieves having a Constraint Index of 1 to 12 can be used. The term "Constraint Index" and a method of its determination are described fully in U.S. Pat. No. 4,016,218, incorporated herein by reference for details of the method.

ZSM-5-type catalysts can be used. Platinum has been found to be particularly useful for promoting dehydrogenation over zeolite catalysts. Of the platinum-containing zeolite catalysts, Sn- and In-containing zeolites are particularly preferred. Sn-containing zeolites, specifically ZSM-5, are taught in U.S. Pat. No. 4,990,710. In-containing zeolites, specifically In-ZSM-5, are taught in U.S. Pat. No. 4,868,145. Both patents are incorporated by reference as if set forth at length herein.

U.S. Pat. No. 9,598,649, hereby incorporated by reference, discloses Pt—Sn-ZSM-5 catalysts that can be used in the presently disclosed methods and systems.

Products

The major product of the integrated process described herein is a $C_{5+}$ hydrocarbon product with a low benzene content making it highly attractive as a gasoline and/or distillate blending stock. Thus, typically the reaction product withdrawn from the first reaction zone of the instant process comprises at least 30 wt %, preferably at least 50 wt % less benzene than the product made by dehydrocyclizing only a paraffinic feed under the conditions in the second reaction zone. Preferably, the $C_{5+}$ product of the presently disclosed process contains less than 1 wt % benzene.

An important aspect of the present process is that, unlike isoparaffin alkylation technologies, this technology allows conversion of all $C_{2+}$ paraffins and $C_{2+}$ olefins and is in many embodiments tolerant to all usual contaminants in such feeds, and in many embodiments additionally or alternatively converts sulfur and nitrogen in a feed to $H_2S$ and $NH_3$.

Also unlike existing paraffins upgrading technologies, the process flow and the associated apparatus are configured to provide direct heat input into the endothermic reaction, making the endotherm portion of the process less expensive and the overall refining process more efficient. The heat input can be adjusted by burning more or less coke or an additional fuel, for example a fuel gas (natural gas), in the catalyst regenerator (comprising at least one regeneration zone) as the catalyst circulation is adjusted to maintain required reaction severity, including flow rate (WHSV) and temperature, to regenerate the catalyst.

Referring now to FIG. 1, the process flow and an associated apparatus for conducting the process steps of one embodiment of the invention are shown. In FIG. 1, an olefin-containing feed 1 is fed to an oligomerization reactor 2. The oligomerization reactor is preferably a fluidized bed reactor or can be configured as a riser reactor. A reaction product stream is withdrawn from the oligomerization reactor 2 via a product effluent transport line 3 and sent to a recovery unit 4. The recovery section can be a fractionator for separating the product into a $C_{5+}$ liquid product stream, a Liquified Petroleum Gas (LPG) liquid product stream and a (vaporous) fraction $C_{2-}$ product stream.

Spent catalyst is removed from the oligomerization reactor 2 and carried through a spent catalyst transport line 5 to a catalyst regenerator 6, where it is contacted with an oxygen-containing stream 7, typically air. A hydrocarbon fuel, such as one or both of $C_{2-}$ and LPG recycled from the recovery unit 4, is also supplied to the regenerator 6 via an inlet so as to raise the temperature of the catalyst in the regenerator to that required for paraffin conversion.

The regenerated catalyst is removed from the regenerator 6 by a regenerated catalyst transport line 8 and contacted with a paraffinic feed 9 in a second reaction zone 10, which can be a mixing point and line transporting the regenerated catalyst and paraffinic feed to the oligomerization reactor 2.

EMBODIMENTS

Further illustrative, non-exclusive embodiments of methods according to the present disclosure are presented in the following enumerated paragraphs.

Embodiment 1

A process for upgrading paraffins and olefins, the process comprising:
(i) contacting a first feed comprising $C_{14-}$ olefins with an oligomerization catalyst in a first reaction zone under conditions effective for oligomerization of olefins to higher molecular weight hydrocarbons;
(ii) removing deactivated catalyst from the first reaction zone at a first temperature;
(iii) contacting the deactivated catalyst with an oxygen-containing gas and with a hydrocarbon-containing fuel in a regeneration zone to regenerate the catalyst and raise the temperature of the catalyst to a second, higher temperature;
(iv) contacting a second feed comprising $C_{14-}$ paraffins with the regenerated catalyst in a second reaction zone to convert at least some of the paraffins in the second feed to a reaction effluent comprising olefins, aromatic hydrocarbons and regenerated catalyst; and
(v) supplying the reaction effluent to the first reaction zone.

Embodiment 2

The process of Embodiment 1 wherein the first reaction zone comprises a fluidized catalyst bed or a riser reactor.

Embodiment 3

The process of Embodiment 1 or 2, wherein the second reaction zone comprises a transfer line for supplying the second feed to the first reaction zone.

Embodiment 4

The process of any one of Embodiments 1-3, in which the contacting (i) is performed at a temperature from 600 to 900° F. (316 to 482° C.).

Embodiment 5

The process of any one of Embodiments 1-4, in which the contacting (i) is performed at a pressure of from 20-400 psig (240 to 2860 kPa-a).

Embodiment 6

The process of any one of Embodiments 1-5, in which the contacting (iii) is performed at a temperature from 1200 to 1450° F. (648 to 788° C.).

Embodiment 7

The process of any one of Embodiments 1-6, in which the contacting (iv) is performed at a temperature from 950-1250° F. (510 to 677° C.).

Embodiment 8

The process of any one of Embodiments 1-7, in which the oligomerization catalyst comprises a molecular sieve.

Embodiment 9

The process of any one of Embodiments 1-8, in which the oligomerization catalyst comprises a molecular sieve having a Constraint Index of 1 to 12.

Embodiment 10

The process of any one of Embodiments 1-9, in which the first feed comprises FCC fuel gas and the second feed comprises $C_3$ to $C_5$ paraffins.

Embodiment 11

The process of any one of Embodiments 1-10, in which the contacting (i) also effects alkylation of aromatics in the reaction effluent with olefins in the first feed and/or olefins in the reaction effluent.

Embodiment 12

The process of any one of Embodiments 1-11, further comprising withdrawing a product stream from the first reaction zone.

Embodiment 13

The process of any one of Embodiments 1-12, in which the product stream comprises gasoline and/or distillate boiling range hydrocarbons.

Embodiment 14

The process of any one of Embodiments 1-13, in which the product stream contains at least 30 weight % less benzene than the reaction effluent.

Embodiment 15

The process of any one of Embodiments 1-14, in which the fuel comprises one or both of liquid petroleum gas (LPG) or $C_{2-}$ hydrocarbon gas recovered from a product stream withdrawn from the first reaction zone.

Embodiment 16

The process of any one of Embodiments 1-16, in which the weight ratio of the amount of $C_{14-}$ olefins in the first feed to the amount of $C_{14-}$ paraffins in the second feed is at least 1:1.

Embodiment 17

A system for upgrading paraffins and olefins comprising:
an oligomerization reactor containing a fluidized catalyst and configured with separate inlets to receive a converted paraffin feed stream comprising regenerated catalyst and a fresh olefin feed stream and further configured with separate outlets for a product stream and a spent catalyst stream;
a catalyst regenerator configured with an inlet to receive a spent catalyst stream from the oligomerization reactor, an inlet for an oxidant gas, and an inlet for receiving a fuel and configured with an outlet for a regenerated catalyst stream; and
a mixing zone configured to combine a fresh paraffinic feed stream with the regenerated catalyst stream and having an outlet for a converted paraffin feed stream; and
a transfer line connecting the mixing zone to the converted paraffin feed stream inlet of the oligomerization reactor.

Embodiment 18

The system of Embodiment 17, that further comprises a recovery unit operably connected to the oligomerization reactor for receiving the product stream, the recovery unit configured to separate and recover a $C_{5+}$ hydrocarbon product, a liquified petroleum gas (LPG) product, and a $C_{2-}$ hydrocarbon gas product.

Embodiment 19

The system of Embodiment 18, that further comprises a transport line to recycle one or more of LPG or $C_{2-}$ hydrocarbons from the recovery unit to the fuel inlet of the catalyst regenerator.

Embodiment 20

A $C_{5+}$ hydrocarbon product produced by integrating a process of oligomerizing an olefinic feed under a first set of conditions and a process of dehydrocyclizing a paraffinic feed under a second set of conditions, the product containing less benzene than would be produced by dehydrocyclizing the paraffinic feed alone under the second set of conditions.

Embodiment 21

The $C_{5+}$ hydrocarbon product of Embodiment 20 that contains at least 30 weight % less benzene than would be produced by dehydrocyclizing the paraffinic feed alone under the second set of conditions.

Embodiment 22

The $C_{5+}$ hydrocarbon product of Embodiment 21 that contains less than 1 wt. % benzene.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:
1. A process for upgrading paraffins and olefins, the process comprising:
 (i) contacting a first feed comprising $C_{14-}$ olefins with an oligomerization catalyst in a first reaction zone under conditions effective for oligomerization of olefins to higher molecular weight hydrocarbons;
 (ii) removing deactivated catalyst from the first reaction zone at a first temperature;
 (iii) contacting the deactivated catalyst with an oxygen-containing gas and with a hydrocarbon-containing fuel in a regeneration zone to regenerate the catalyst and raise the temperature of the catalyst to a second, higher temperature;
 (iv) contacting a second feed comprising $C_{14-}$ paraffins with the regenerated catalyst in a second reaction zone to convert at least some of the paraffins in the second feed to a reaction effluent comprising olefins, aromatic hydrocarbons and regenerated catalyst;
 (v) supplying the reaction effluent to the first reaction zone; and
 (vi) withdrawing a product stream from the first reaction zone; wherein the product stream contains at least 30 weight % less benzene than the reaction effluent.
2. The process of claim 1 wherein the first reaction zone comprises a fluidized catalyst bed or a riser reactor.

3. The process of claim 1 wherein the second reaction zone comprises a transfer line for supplying the second feed to the first reaction zone.

4. The process of claim 1, in which the contacting (i) is performed at a temperature from 600 to 900° F. (316 to 482° C.).

5. The process of claim 1, in which the contacting (i) is performed at a pressure of from 20-400 psig (240 to 2860 kPa-a).

6. The process of claim 1, in which the contacting (iii) is performed at a temperature from 1200 to 1450° F. (648 to 788° C.).

7. The process of claim 1, in which the contacting (iv) is performed at a temperature from 950-1250° F. (510 to 677° C.).

8. The process of claim 1, in which the oligomerization catalyst comprises a molecular sieve.

9. The process of claim 1, in which the oligomerization catalyst comprises a molecular sieve having a Constraint Index of 1 to 12.

10. The process of claim 1, in which the first feed comprises FCC fuel gas and the second feed comprises $C_3$ to $C_5$ paraffins.

11. The process of claim 1, in which the contacting (i) also effects alkylation of aromatics in the reaction effluent with olefins in the first feed and/or olefins in the reaction effluent.

12. The process of claim 1, in which the product stream comprises gasoline and/or distillate boiling range hydrocarbons.

13. The process of claim 1, in which the fuel comprises one or both of liquid petroleum gas (LPG) or $C_{2-}$ hydrocarbon gas recovered from a product stream withdrawn from the first reaction zone.

14. The process of claim 1, in which the weight ratio of the amount of $C_{14-}$ olefins in the first feed to the amount of $C_{14-}$ paraffins in the second feed is at least 1:1.

* * * * *